(12) United States Patent
Hebrank et al.

(10) Patent No.: US 6,750,954 B2
(45) Date of Patent: Jun. 15, 2004

(54) SYSTEMS AND METHODS FOR RAPIDLY AND ACCURATELY INDENTIFYING LIVE EGGS WITHIN A STREAM OF EGGS

(75) Inventors: John H. Hebrank, Durham, NC (US); Thomas Bryan, Raleigh, NC (US)

(73) Assignee: Embrex, Inc., Durham, NC (US)

( * ) Notice: Subject to any disclaimer, the term of this patent is extended or adjusted under 35 U.S.C. 154(b) by 0 days.

(21) Appl. No.: 10/621,170

(22) Filed: Jul. 16, 2003

(65) Prior Publication Data

US 2004/0065263 A1 Apr. 8, 2004

Related U.S. Application Data

(60) Provisional application No. 60/417,003, filed on Oct. 8, 2002.

(51) Int. Cl.[7] .................. A01K 43/00; G01N 33/08
(52) U.S. Cl. .................. 356/53; 356/54; 356/59
(58) Field of Search .................. 356/52, 53, 58, 356/59, 66; 209/510, 511

(56) References Cited

U.S. PATENT DOCUMENTS

| | | | |
|---|---|---|---|
| 2,762,365 A | 9/1956 | Wagner et al. .................. 128/1 |
| 3,037,479 A | 6/1962 | Flory .................. 119/1 |
| 3,377,989 A | 4/1968 | Sandhage .................. 119/1 |
| 3,420,743 A | 1/1969 | Sandhage .................. 195/104 |
| 3,506,140 A | 4/1970 | Koch et al. .................. 214/1 |
| 3,594,285 A | 7/1971 | Noren .................. 195/127 |
| 3,616,262 A | 10/1971 | Coady et al. .................. 195/127 |
| 4,040,388 A | 8/1977 | Miller .................. 119/1 |
| 4,458,630 A | 7/1984 | Sharma et al. .................. 119/1 |
| 4,469,047 A | 9/1984 | Miller .................. 119/1 |
| 4,593,646 A | 6/1986 | Miller et al. .................. 119/1 |
| 4,671,652 A | 6/1987 | van Asselt et al. .................. 356/66 |
| 4,681,063 A | 7/1987 | Hebrank .................. 119/1 |
| 4,903,635 A | 2/1990 | Hebrank .................. 119/1 |
| 4,914,672 A * | 4/1990 | Hebrank .................. 374/124 |
| 4,928,628 A | 5/1990 | Gassman et al. .................. 119/1 |
| 4,928,629 A | 5/1990 | Trampel .................. 119/1 |
| 4,955,728 A | 9/1990 | Hebrank .................. 374/124 |
| 5,028,421 A | 7/1991 | Fredericksen et al. .................. 424/85.2 |
| 5,056,464 A | 10/1991 | Lewis .................. 119/6.8 |
| 5,136,979 A | 8/1992 | Paul et al. .................. 119/6.8 |
| 5,158,038 A | 10/1992 | Sheeks et al. .................. 119/6.8 |
| 5,173,737 A | 12/1992 | Mitchell et al. .................. 356/53 |
| 5,176,101 A | 1/1993 | Paul et al. .................. 119/6.8 |
| 5,745,228 A | 4/1998 | Hebrank et al. .................. 356/53 |
| RE35,973 E | 12/1998 | Paul et al. .................. 119/6.8 |
| 6,032,612 A | 3/2000 | Williams .................. 119/6.8 |
| 6,145,668 A | 11/2000 | DePauw et al. .................. 209/510 |
| 6,149,375 A | 11/2000 | Hebrank .................. 414/737 |
| 6,213,709 B1 | 4/2001 | Hebrank .................. 414/737 |
| 6,224,316 B1 | 5/2001 | Hebrank et al. .................. 414/404 |
| 6,234,320 B1 * | 5/2001 | Hebrank .................. 209/510 |
| 6,535,277 B2 * | 3/2003 | Chalker et al. .................. 356/53 |

* cited by examiner

*Primary Examiner*—Frank G. Font
*Assistant Examiner*—Roy M. Punnoose
(74) *Attorney, Agent, or Firm*—Myers Bigel Sibley & Sajovec

(57) ABSTRACT

Systems and methods for rapidly identifying live eggs within a stream of eggs with high accuracy, are provided. A stream of eggs are candled via a candling apparatus and each candled egg is designated as being either live, non-live, or "uncertain". Eggs designated as non-live and uncertain are removed from the stream. Each egg designated as uncertain is "recandled" at a separate station via an additional candling procedure in order to definitively determine if the "uncertain" egg is live or non-live. Uncertain eggs identified as being live via recandling are returned to the egg stream such that the stream contains only live eggs. The uncertain eggs determined to be non-live via recandling are removed and are either discarded or used for other purposes.

30 Claims, 9 Drawing Sheets

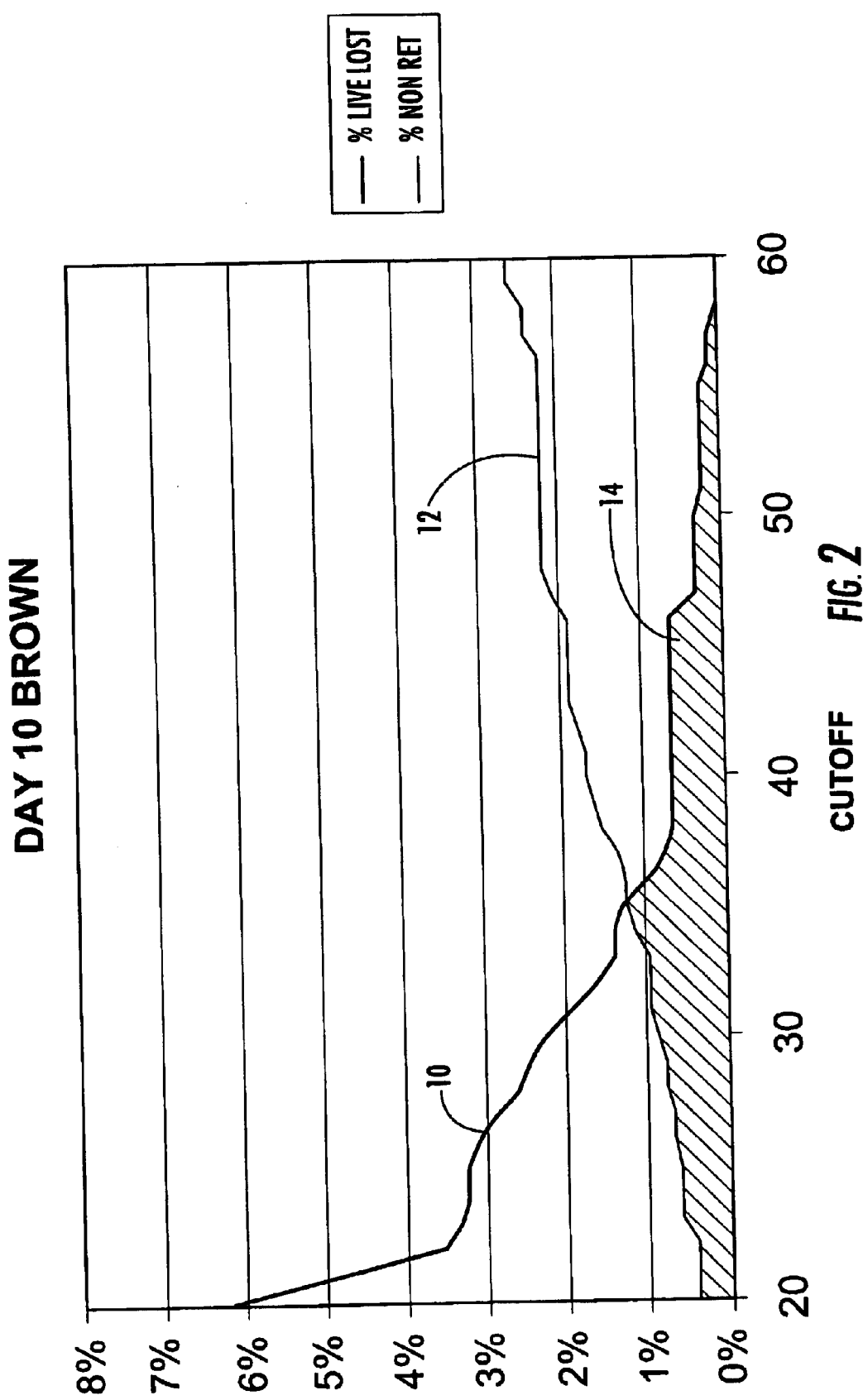

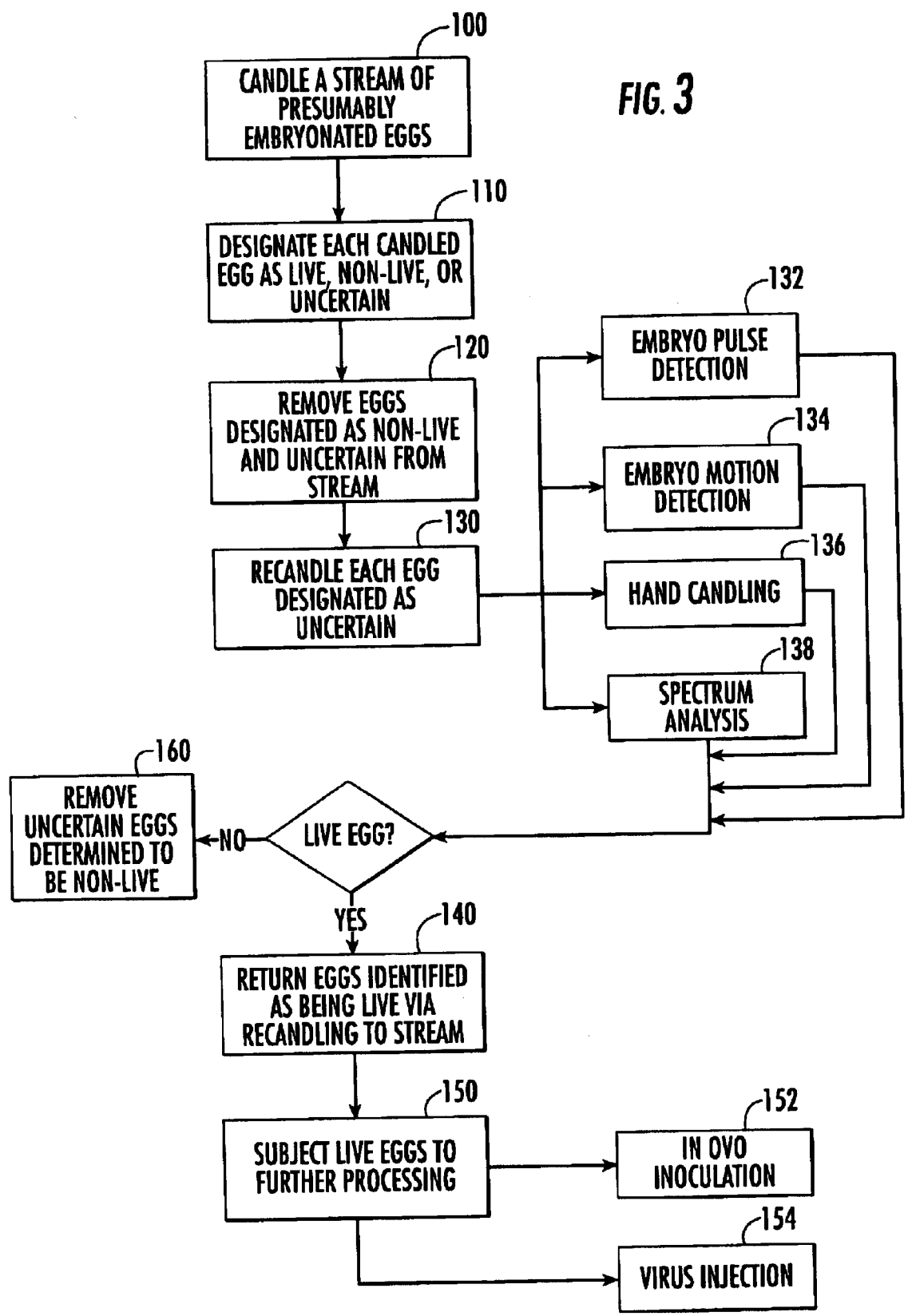

SYSTEMS AND METHODS FOR RAPIDLY AND ACCURATELY INDENTIFYING LIVE EGGS WITHIN A STREAM OF EGGS

RELATED APPLICATION

This application claims the benefit of U.S. Provisional Application No. 60/417,003 filed Oct. 8, 2002, the disclosure of which is incorporated herein by reference in its entirety as if set forth fully herein.

FIELD OF THE INVENTION

The present invention relates generally to eggs and, more particularly, to methods and apparatus for processing eggs.

BACKGROUND OF THE INVENTION

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with eggs, although egg shells appear opaque under most lighting conditions, they are in reality somewhat translucent, and when placed in front of direct light, the contents thereof can be observed.

An egg may be a "live" egg, meaning that it has a viable embryo. FIG. 1A illustrates a live poultry egg 1 at about day one of incubation. FIG. 1B illustrates the live egg 1 at about day eleven of incubation. The egg 1 has a somewhat narrow end in the vicinity represented at 1a as well as an oppositely disposed broadened end portion in the vicinity shown at 1b. In FIG. 1A, an embryo 2 is represented atop the yolk 3. The egg 1 contains an air cell 4 adjacent the broadened end 1b. As illustrated in FIG. 1B, the wings 5, legs 6, and beak 7 of a baby chick have developed.

An egg may be a "clear" or "infertile" egg, meaning that it does not have an embryo. More particularly, a "clear" egg is an infertile egg that has not rotted. An egg may be an "early dead" egg, meaning that it has an embryo which died at about one to five days old. An egg may be a "mid-dead" egg, meaning that it has an embryo which died at about five to fifteen days old. An egg may be a "late-dead" egg, meaning that it has an embryo which died at about fifteen to eighteen days old.

An egg may be a "rotted" egg, meaning that the egg includes a rotted infertile yolk (for example, as a result of a crack in the egg's shell) or, alternatively, a rotted, dead embryo. While an "early dead", "mid-dead" or "late-dead egg" may be a rotted egg, those terms as used herein refer to such eggs which have not rotted. Clear, early-dead, mid-dead, late-dead, and rotted eggs may also be categorized as "non-live" eggs because they do not include a living embryo.

Eggs which are to be hatched to live poultry are typically candled during embryonic development to identify clear, rotted, and dead eggs (collectively referred to herein as "non-live eggs"). Non-live eggs are removed from incubation to increase available incubator space. In many instances it is desirable to introduce a substance, via in ovo injection, into a live egg prior to hatch. Injections of various substances into avain eggs are employed in the commercial poultry industry to decrease post-hatch mortality rates or increase the growth of the hatched bird. Similarly, the injection of virus into live eggs is utilized to propagate virus for use in preparing vaccines. Examples of substances that have been used for, or proposed for, in ovo injection include vaccines, antibodies and vitamins. Examples of in ovo treatment substances and methods of in ovo injection are described in U.S. Pat. No. 4,458,630 to Sharma et al., the contents of which are hereby incorporated by reference as if recited in full herein.

In ovo injections of substances typically occur by piercing an egg shell to create a hole therethrough (e.g., using a punch or drill), extending an injection needle through the hole and into the interior of the egg (and in some cases into the avain embryo contained therein), and injecting one or more treatment substances through the needle. An example of an injection device is disclosed in U.S. Pat. No. 4,681,063 to Hebrank; this device positions an egg and an injection needle in a fixed relationship to each other, and is designed for the high-speed automated injection of a polarity of eggs. The selected of both the site and time of injection treatment can also impact the effectiveness of the injected substance, as well as the mortality rate of the injected eggs or treated embryos. See, for example, U.S. Pat. No. 4,458,630 to Sharma et al., U.S. Pat. No. 4,681,063 to Hebrank, and U.S. Pat. No. 5,158,038 to Sheeks et al. U.S. Pat. No. 5,158,038 to Sheeks et al., U.S. Patents cited herein are hereby incorporated by reference herein in their entireties.

In commercial poultry production, only about 60% to 90% of commercial broiler eggs hatch. Eggs that do not hatch include eggs that were not fertilized, as well as fertilized eggs that have died. Infertile eggs may comprise from about 5% up to about 50% of all eggs in a set. Due to the number of non-live eggs encountered in commercial poultry production, the increasing use of automated methods for in ovo injection, and the cost of treatment substances, an automated method for identifying live eggs and selectively injecting only live eggs, is desirable.

There are other applications where it is important to be able to distinguish between live and nonlive eggs. One of these applications is the cultivation and harvesting of human flu vaccines via live eggs (referred to as "vaccine production eggs"). Human flu vaccine production is accomplished by injecting seed virus into a chicken egg at about day eleven of embryonic development (Day-11 egg), allowing the virus to grow for about two days, euthanizing the embryo by cooling the egg, and then harvesting the amniotic fluid from the egg. Typically, eggs are candled before injection of a seed virus to remove non-live eggs. Vaccine production eggs may be candled one or more days prior to injection of a seed virus therein. It is desirable to prevent seed vaccine from being wasted in non-live eggs and to eliminate costs associated with transporting and disposing of non-live eggs.

U.S. Pat. No. 3,616,262 to Coady et al. discloses a conveying apparatus for eggs that includes a candling station and an inoculation station. At the candling station, light is projected through the eggs and assessed by a human operator, who marks any eggs considered non-live. Non-live eggs are manually removed before the eggs are conveyed to the inoculating station.

U.S. Pat. Nos. 4,955,728 and 4,914,672, both to Hebrank, describe a candling apparatus that uses infrared detectors and the infrared radiation emitted from an egg to distinguish live from infertile eggs. U.S. Pat. No. 4,671,652 to van Asselt et al. describes a candling apparatus in which a plurality of light sources and corresponding light detectors are mounted in an array, and wherein eggs are passed on a flat between the light sources and the light detectors.

Unfortunately, conventional candling techniques may have somewhat limited accuracy, especially at high candling through-put speeds. Pulsed light opacity identification systems can operate at speeds equivalent to about 300,000 eggs per hour and successfully identify clear eggs from a stream of eggs. However, some eggs identified as being live will in fact be non-live (e.g., rotted eggs, mid and late dead eggs).

Thermal-based candling systems can detect rotted eggs in egg streams of up to 50,000 eggs per hour. In the candling method and apparatus described in U.S. Pat. No. 4,914,672 to Hebrank, for example, a thermal candling system measures the temperature of each egg from the bottom. The thermal candling system determines a threshold temperature. Eggs above the threshold temperature are deemed live and eggs below the threshold temperature are deemed non-live (which includes dead and clear eggs). Unfortunately, because of egg-to-egg thermal variations, thermal-based candling systems may misidentify live and non-live eggs.

FIG. 2 illustrates exemplary light value curves for live eggs and non-live eggs as measured via a light opacity candling system. Curve 10 is an upper end of a Gaussian-like cumulative distribution of light values for live eggs, and curve 12 is a lower end of a Gaussian-like cumulative distribution of light values for non-live eggs. The shaded area 14 represents a mixture of live eggs and non-live eggs in a stream of eggs because of overlapping light values. In other words, a live egg may have a light value, for example, of thirty (30), but a non-live egg may also have a light value of thirty (30). The candling system producing these light value curves cannot identify whether an egg having a light value within the range of the shaded area 14 is live or non-live.

Pulse detection methods are known that can detect live eggs with a high degree of accuracy. For example, Buddy by Avitronics (Truro, England) can reliably detect embryo heartbeats. Detection happens in about five to ten seconds for about 60% of eggs, with near 100% detection requiring 60 second sampling times. Unfortunately, the time required to detect a live egg is prohibitively slow for use in hatcheries where high through-put rates are required. For automated pulse detection to be a useful method of determining viable eggs, a much shorter processing time is needed to read hatchery volumes of eggs (typically several hundred thousand in six to eight hours).

A more recent development of pulse detection technology uses heartbeat or embryo motion to detect live eggs and can operate up to 500 eggs per hour per sensing device.

U.S. Pat. No. 5,173,737 to Mitchell describes a method of determining whether an egg contains a live embryo by directing light into an egg to stimulate embryo movement, and then measuring resulting embryo movement. Unfortunately, the Mitchell method may be time-consuming and may not accurately detect live embryos that do not move as a result of light stimulation.

SUMMARY OF THE INVENTION

In view of the above discussion, systems and methods of rapidly identifying live eggs within a stream of eggs with high accuracy, are provided. According to an embodiment of the present invention, a stream of presumably embryonated eggs are candled via a candling apparatus (light candling, thermal candling, etc.) and each candled egg is designated as being either live, non-live, or "uncertain". Eggs designated as non-live and uncertain are removed from the stream. Each egg designated as uncertain is "recandled" at a separate station via an additional candling procedure in order to definitively determine if the "uncertain" egg is live or non-live.

According to an embodiment of the present invention, recandling may include embryo pulse detection and/or embryo motion detection. According to another embodiment of the present invention, recandling may include "hand candling" wherein a person manually candles an egg via a light source to determine if the egg is live or non-live. As is understood by those skilled in the art, hand candling typically takes place in a dark room. A light source is held to each egg. If the egg is completely yellow with no dark areas or visible veins then it is classified as 'clear' (infertile or very early dead). Indistinct dark areas or a cloudy or mottled appearance indicates a dead egg. A greenish hued color indicates a likely rotten egg. Live eggs have clearly visible red veins, a distinct air cell circle at the top (blunt) end of the egg and an identifiable dark embryonic area. Movement may be seen. In addition, human candlers pick out cracked eggs, upside down embryos and eggs with side air cells.

According to another embodiment of the present invention, recandling may include generating a light intensity spectrum of light passing through an egg and comparing the spectrum with a spectrum associated with a live egg.

Uncertain eggs identified as being live via recandling are returned to the egg stream such that the stream contains only live eggs. The live eggs may then be subjected to further processing, such as in ovo injection of a vaccination or other inoculation or virus injection. The uncertain eggs determined to be non-live via recandling are removed and are either discarded or used for other purposes.

BRIEF DESCRIPTION OF THE DRAWINGS

The accompanying drawings, which form a part of the specification, illustrate key embodiments of the present invention. The drawings and description together serve to fully explain the invention.

FIG. 2 illustrates overlapping light value curves for live eggs and non-live eggs.

FIG. 3 is a flowchart of operations for rapidly and accurately identifying live eggs in a stream of eggs, according to embodiments of the present invention.

DETAILED DESCRIPTION OF THE INVENTION

Figure 1B:
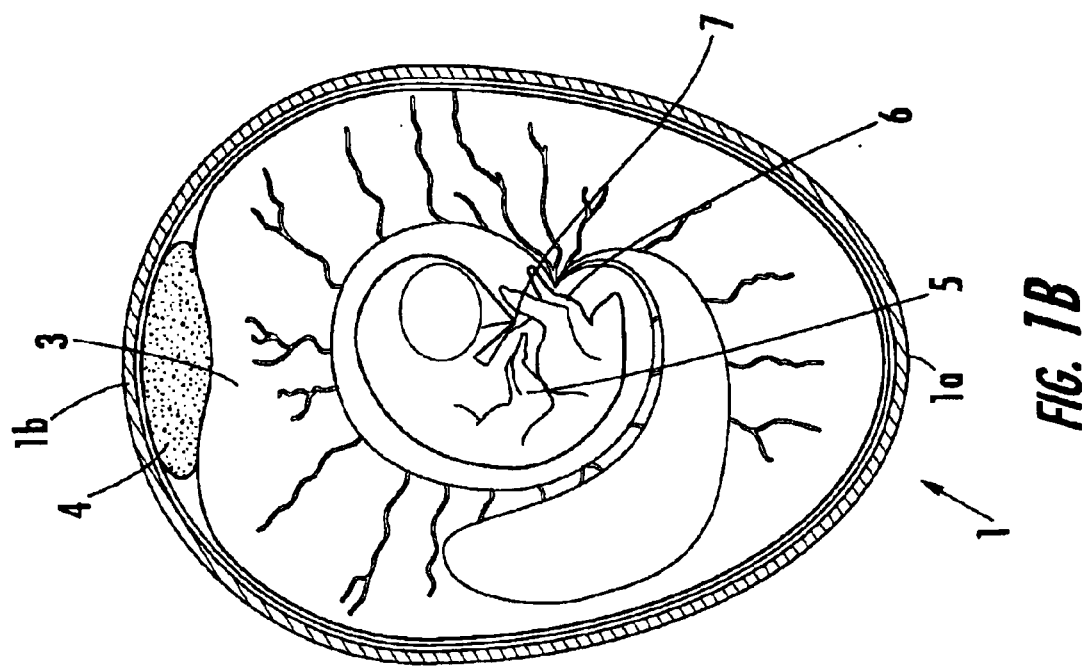
FIG. 1B illustrates a live chicken egg at about day eleven of incubation.
Figure 1A:
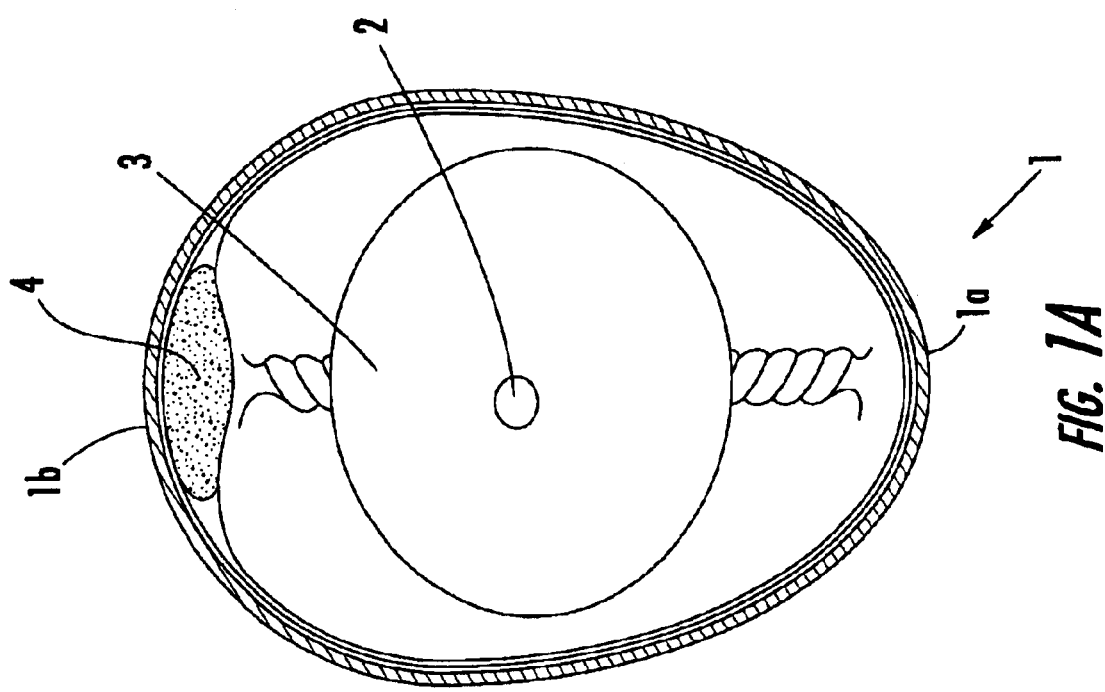
FIG. 1A illustrates a live chicken egg at about day one of incubation.

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Systems and methods according to embodiments of the present invention may be utilized for rapidly and accurately identifying live and non-live eggs at any time during embryonic development (also referred to as the incubation period). Embodiments of the present invention are not limited to identification at a particular day (e.g., day eleven) during the embryonic development period. In addition, systems and methods according to embodiments of the present invention may be used with any types of avian eggs, including chicken, turkey, duck, geese, quail, pheasant eggs, exotic bird eggs, etc.

Referring now to FIG. 3, methods of rapidly identifying live eggs within a stream of eggs with high accuracy, according to embodiments of the present invention, are illustrated. Initially, a stream of presumably embryonated eggs are candled via a candling apparatus (Block 100) and each candled egg is designated as being either live, non-live, or "uncertain" (Block 110). The term "uncertain" means that the candling procedure cannot determine with certainty whether an egg is live or non-live.

Candling may include light candling, thermal candling or a combination of light and thermal candling, For example as described in U.S. Pat. No. 6,234,320 to Hebrank, which is incorporated herein by reference in its entirety. As is known to those skilled in the art, light candling involves measuring the opacity of an egg by illuminating the egg with light from a light source, and measuring the amount of light passing through the egg at a detector positioned adjacent the egg. According to embodiments of the present invention, an egg is designated as live if the measured opacity is less than a first threshold value, and egg is designated as non-live if the measured opacity is greater than a second threshold value, and an egg is designated as uncertain if the measured opacity is between the first and second threshold value.

As is known to those skilled in the art, thermal candling involves measuring the temperature of an egg. According to embodiments of the present invention, an egg is designated as live if the measured temperature is above a first threshold temperature, an egg is designated as non-live if the measured temperature is lower than a second threshold temperature, and an egg is designated as uncertain if the measured temperature is between the first and second temperatures.

Various candling operations known to those skilled in the art, including combinations of candling operations, may be utilized to carry out operations represented by Block 100.

Eggs designated as non-live and uncertain are removed from the stream (Block 120). The non-live eggs are either discarded or used for other purposes. Each egg designated as uncertain is "recandled" at a separate station via an additional candling procedure in order to determine if the "uncertain" egg is live or non-live (Block 130). The term "recandled" is intended to include any of various procedures (or combinations of various procedures) for determining whether or not an egg is live or non-live.

Figure 4:
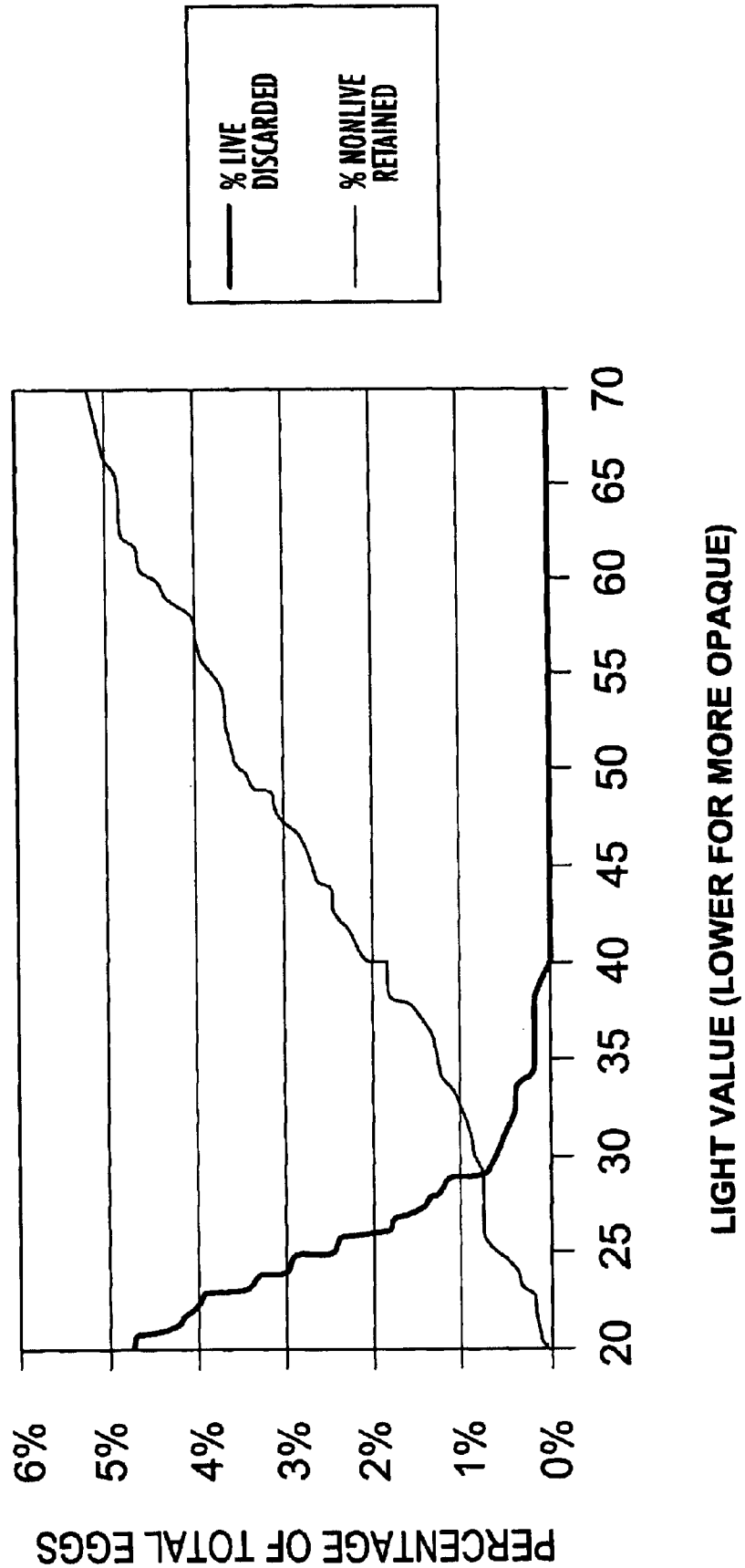
FIG. 4 illustrates overlapping light value curves for Day 11 brown eggs.

FIG. 4 illustrates light values for Day 11 brown eggs. As shown, 99.8% of the live eggs have light values below 35, about 4.5% of the live eggs have light values between 20 and 35, virtually no non-live eggs have light values less than 20, and about 1.5% of all eggs are non-live with light values between 20 and 35. According to embodiments of the present invention, all eggs having light values greater than 35 are clear eggs and are removed and discarded from the stream of eggs (Block 120). All eggs having light values between 20 and 35 are designated "uncertain" and are removed and subjected to recandling (e.g., pulse detection, hand candling, spectrum analysis, or embryo motion detection) (Block 130).

Recandling may include embryo pulse detection (Block 132). According to an embodiment of embryo pulse detection, each egg designated as uncertain is illuminated with light from one or more selected portions of the spectrum via a light source positioned adjacent the egg. The intensity of light leaving an uncertain egg via a photodetector is measured and an output signal that corresponds to detected light intensity is generated. The output signal is then processed to identify cyclical and non-cyclical variations in light intensity. An uncertain egg is designated as a live egg in response to identifying cyclical variations in light intensity since cyclical variations in light intensity may indicate the existence of an embryo pulse.

Recandling may include detecting embryonic motion within an egg (Block 134). For example, non-cyclical variations in light intensity detected during pulse rate detection may indicate embryo movement. Thus, an uncertain egg may be designated as a live egg in response to the detection of non-cyclical variations in light intensity.

Recandling may include "hand candling" wherein a person manually candles an egg via a light source to determine if the egg is live (Block 136). Uncertain eggs having clearly visible red veins, a distinct air cell circle at the top (blunt) end of the egg and an identifiable dark embryonic area are designated as live eggs.

In addition, recandling may include generating a light intensity spectrum of light passing through an egg and comparing the spectrum with a spectrum associated with a live egg (Block 138). For example, an uncertain egg may be illuminated with light from a light source and light passing through the egg is received at a detector positioned adjacent the egg. Light may include, but is not limited to, light in both visible and infrared wavelengths. The intensity of the received light is determined and a spectrum is generated that represents the detected light intensity at selected wavelengths. The generated spectrum is compared with a spectrum associated with a live egg. If the uncertain egg has a spectrum that substantially matches the spectrum associated with a live egg, the uncertain egg is designated as a live egg.

Uncertain eggs identified as being live via recandling are returned to the egg stream such that the stream contains only live eggs (Block 140). The live eggs may then be subjected to further processing (Block 150), such as in ovo injection of a vaccination or other inoculation (Block 152) or virus injection (Block 154). The uncertain eggs determined to be non-live via recandling are removed (Block 160) and are either discarded or used for other purposes.

Exemplary egg throughput numbers for embodiments of the present invention may be as follows. A light candler processing 40,000 eggs per hour of a flock having fertility in the 90% to 95% range may designate about 6% of the eggs as uncertain. Accordingly, about 2,400 uncertain eggs would require additional analysis each hour. Hand candling rates are typically about 2,200 to 2,800 eggs per hour per person, and a seven channel embryo pulse detector operating on a ten-second cycle may process about 2,500 eggs per hour. As such, both hand candling and pulse rate detection will likely be able to process uncertain eggs without negatively impacting overall egg processing throughput.

Figure 5:
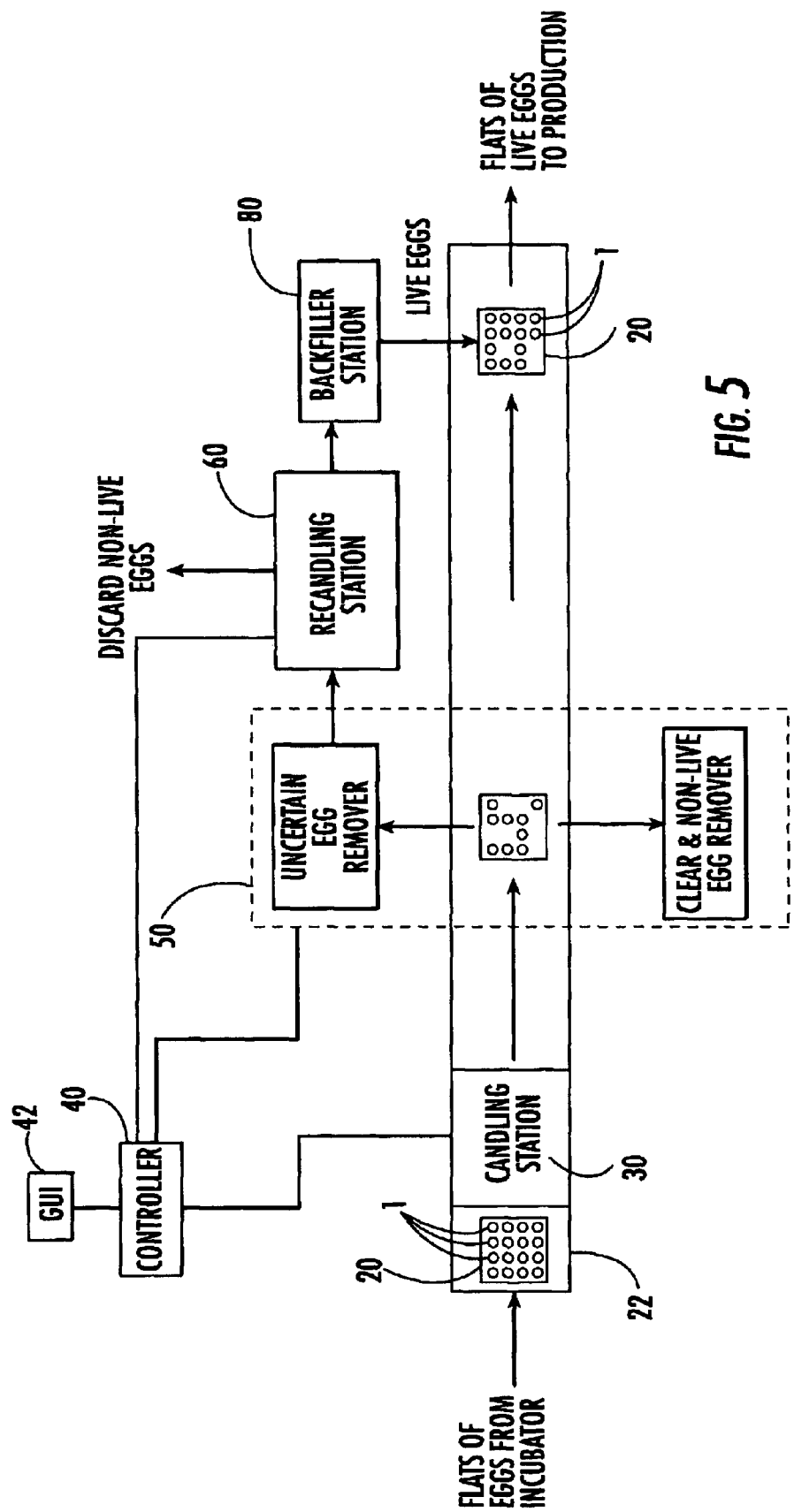
FIG. 5 is a block diagram of a system for separating live and non-live eggs from a plurality of eggs, according to embodiments of the present invention.

FIG. 5 is a block diagram of a system for identifying live eggs from a stream of eggs, according to embodiments of the present invention. A flat 20 of eggs 1 is conveyed via a conveyor 22 to a candling station 30 that is configured to designate each egg 1 within the flat 20 as being either live, non-live, or uncertain. Any type of conveying system suitable for conveying flats of eggs may be utilized in accordance with embodiments of the present invention. Egg conveying systems are well known to those of skill in the art and need not be described further herein.

Although eggs conventionally are carried in egg flats, any means of presenting a stream of eggs over time to a candling station 30, as well as to other egg processing equipment, may be used. Egg flats of virtually any type may be used in accordance with embodiments of the present invention. Flats may contain any number of rows, such as seven rows of eggs, with rows of six and seven being most common. Moreover, eggs in adjacent rows may be parallel to one another, as in a "rectangular" flat, or may be in a staggered relationship, as in an "offset" flat. Examples of suitable commercial flats include, but are not limited to, the "CHICKMASTER 54" flat, the "JAMESWAY 42" flat and the "JAMESWAY 84" flat (in each case, the number indicates the number of eggs carried by the flat). Egg flats are well known to those of skill in the art and need not be described further herein.

The candling station 30 may include a light candling system and/or a thermal candling system. An exemplary light candling system that may be utilized is described in U.S. Pat. No. 5,745,228 to Hebrank et al. which is incorporated herein by reference in its entirety. A suitable commercial light candling system includes the S Beam light candling system of the Vaccine Saver™ vaccine delivery system available from Embrex, Inc. of Research Triangle Park, N.C. An exemplary light and thermal candling system is described in U.S. Pat. No. 6,234,320 to Hebrank, which is incorporated herein by reference in its entirety. Other exemplary thermal candling systems are described in U.S. Pat. No. 4,914,672 and in U.S. Pat. No. 4,955,728, each to Hebrank, each of which is incorporated herein by reference in its entirety. Other suitable devices for measuring the opacities of eggs and/or measuring temperatures of eggs may be used in accordance with embodiments of the present invention. Such other suitable devices will be apparent to those skilled in the art from reading the description herein.

The candling station 30 in the illustrated embodiment is operatively connected to a controller 40 which controls operations of the candling station 30 and stores information received from the candling station 30 about each egg 1. The controller 40 also designates each egg as live, non-live, or uncertain and stores this information. An operator interface (e.g., a display) 42 may be provided to allow an operator to interact with the controller 40. The controller 40 may control various other downstream egg processing operations, as well, including recandling operations.

Eggs designated as non-live and uncertain are removed from the flat 20 downstream from the candling station 30 at egg removal station 50. According to embodiments of the present invention, the controller 40 generates a selective removal signal for eggs determined to be uncertain, clear or non-live. The clear and nonlive eggs are removed from the flat 20 and discarded. Eggs identified as uncertain are transported to a "recandling" station 60, which may include a pulse detection apparatus/system (for detecting embryo pulse and/or embryo motion), a hand candling station, and/or a light spectrum generation and analysis station.

The egg removal station 50 may be a manual station wherein the designated clear, non-live and uncertain eggs are removed by hand. Alternatively, the egg removal station 50 may operate automatically and robotically. For example, the egg removal station 50 may employ suction-type lifting devices as disclosed in U.S. Pat. No. 4,681,063 or in U.S. Pat. No. 5,017,003 to Keromnes et al., the disclosures of which are hereby incorporated by reference in their entireties. Various devices and methods for automatically and robotically removing eggs from a flat and transporting same to another location may be utilized with embodiments of the present invention without limitation. Exemplary egg removal apparatus that may serve the function of the egg removal station 50 are described in U.S. Pat. Nos. 6,145,668; 6,149,375; 6,213,709; and 6,224,316, each of which is incorporated herein by reference in its entirety.

Figure 6A:
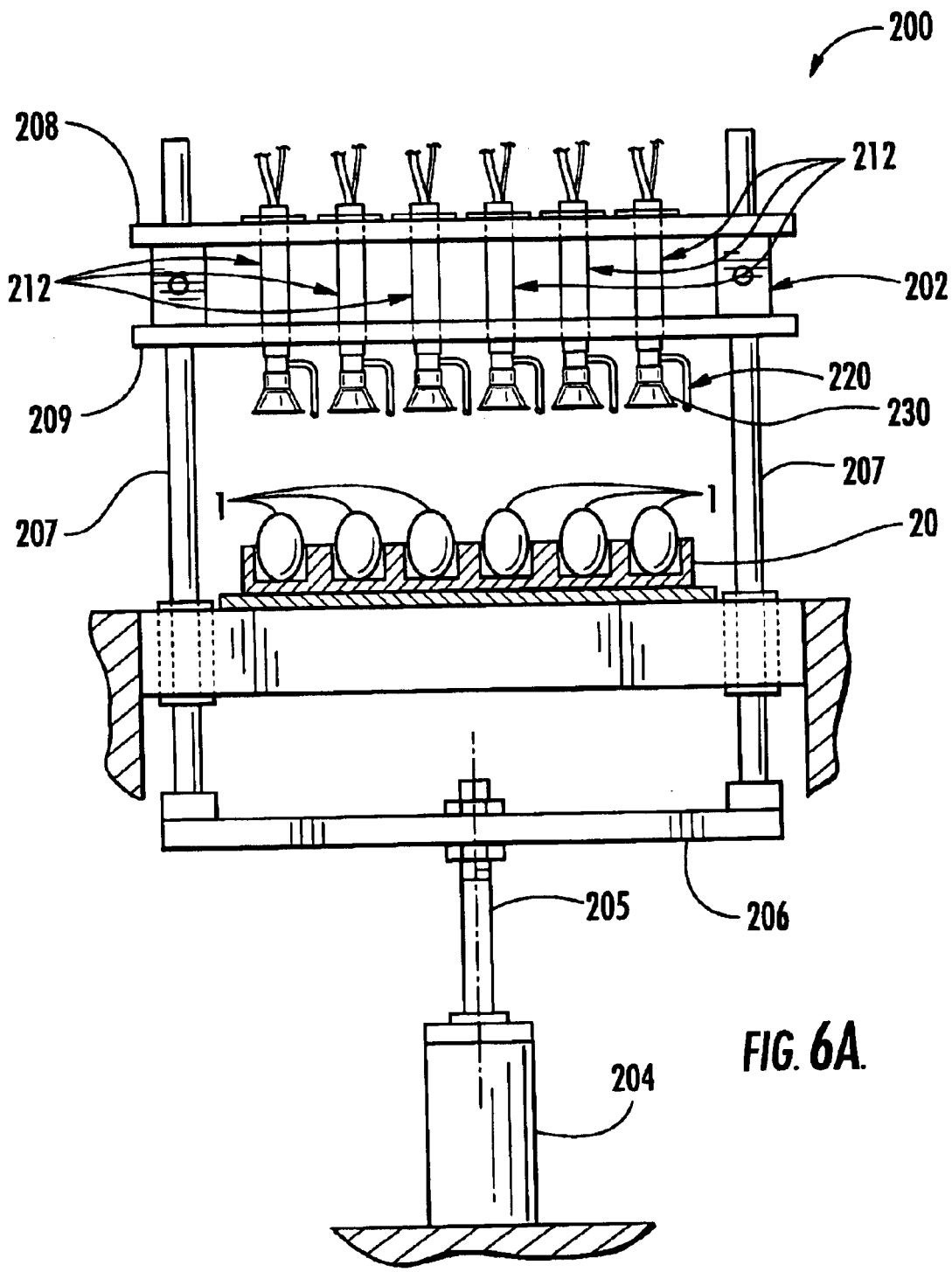
FIG. 6A is a side elevation view of an apparatus for detecting embryo pulse rates and/or motion according to embodiments of the present invention, wherein the frame is in the retracted position.
Figure 6B:
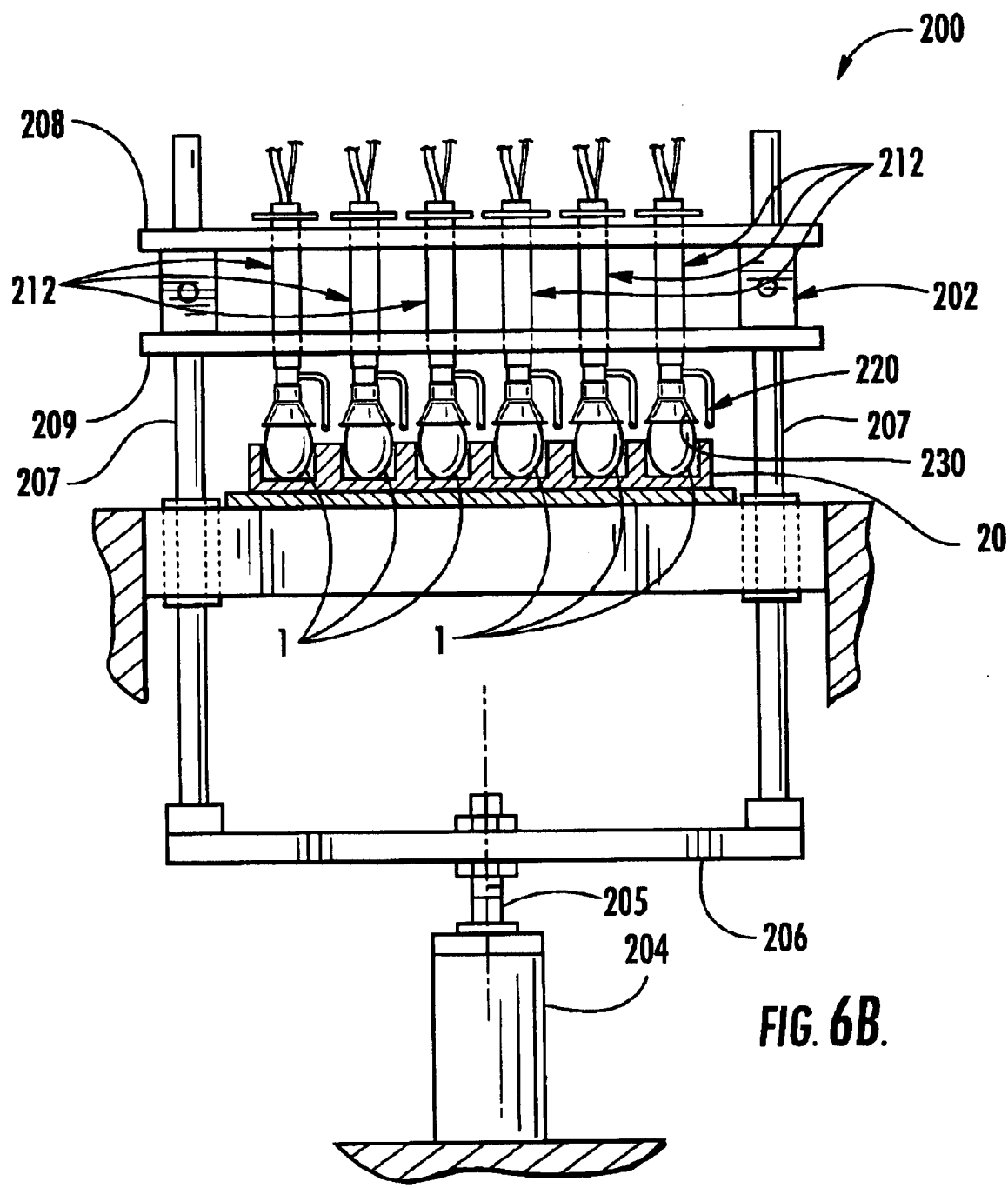
FIG. 6B illustrates the apparatus of FIG. 6A with the frame in the extended position.
Figure 6C:
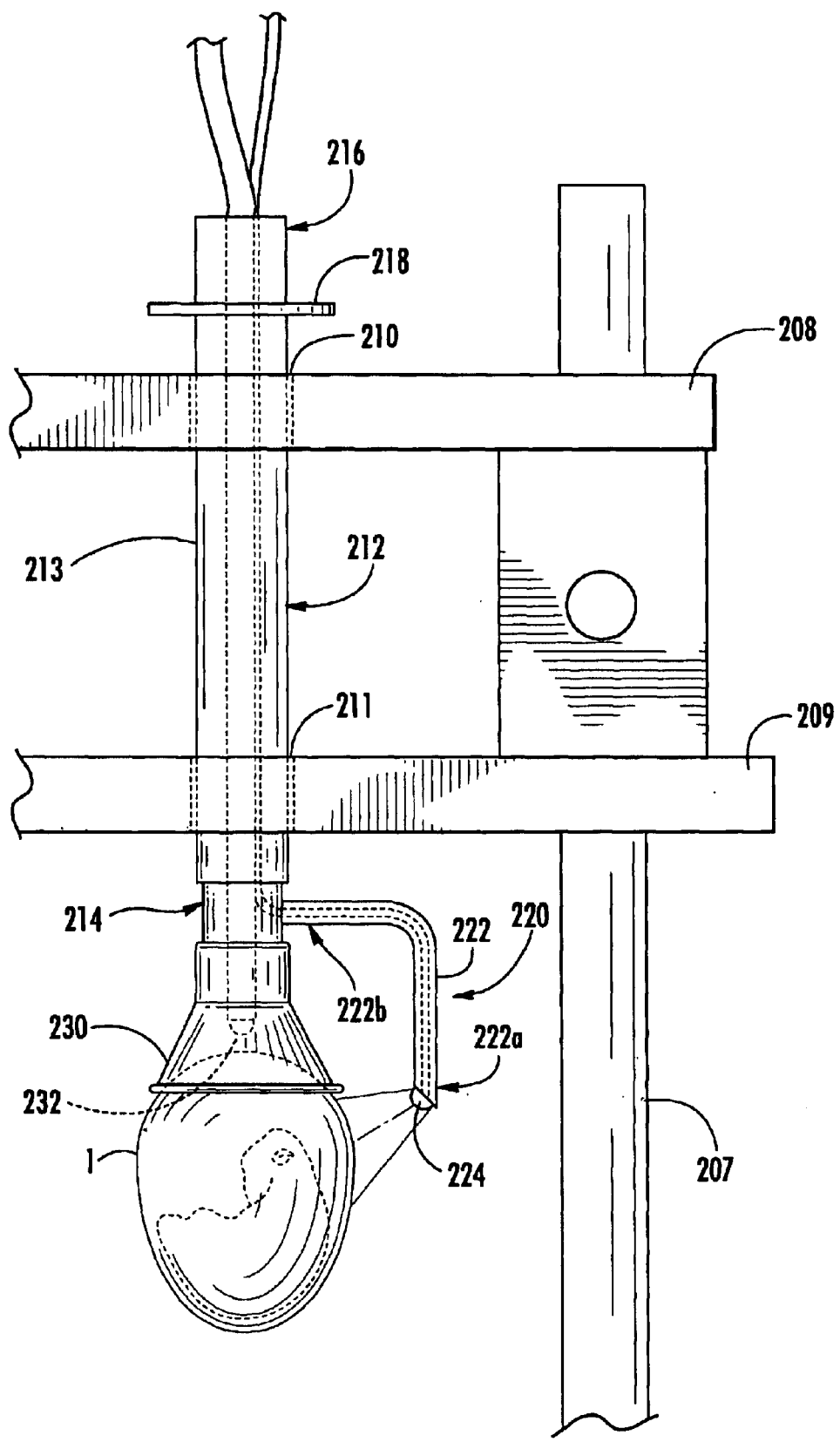
FIG. 6C is an enlarged view of one of the detector tools of FIGS. 6A–6B.

According to embodiments of the present invention, the recandling station 60 may include a pulse detection apparatus, wherein one or more pulse detectors are employed to detect a pulse rate and/or embryonic motion in each of a plurality of uncertain eggs. FIGS. 6A–6C, illustrate an exemplary pulse detection apparatus 200 that may be utilized to detect pulse rates and/or embryonic motion in a plurality of eggs, in accordance with embodiments of the present invention. The illustrated apparatus 200 includes a frame 202 that is movable between a raised position (FIG. 6A) and a lowered position (FIG. 6B). The apparatus 200 includes means, shown as the cylinder 204, cylinder shaft 205, horizontal member 206 and upright shafts 207, for raising and lowering the frame 202 and the detector tools suspended therefrom. However, embodiments of the present invention are not limited to the illustrated means for raising and lowering the frame 202. Various arrangements for raising and lowering frame 202 can be used in accordance with embodiments of the present invention. Moreover, embodiments of the present invention are not limited to the illustrated configuration of frame 202.

The illustrated frame 202 includes upper and lower plates 208, 209 in spaced-apart relationship. Each plate includes a respective array of openings 210, 211 formed therethrough. A plurality of detector tools 212 are supported in a generally vertical orientation via the upper plate 208. Each detector tool 212 has an elongated member 213 that extends through respective openings 210, 211 in the upper and lower plates 208, 209. A lower portion (broadly designated as 214) of each detector tool 212 depends downwardly below the lower plate 209. An upper portion (broadly designated as 216) of each detector tool 212 extends above the upper plate 208. A clip 218 is secured to the upper portion 216 of each detector tool 212. When the frame 202 is in the raised position (FIG. 6A), the upper plate 208 supports the detector tools 212 via respective clips 218. When the frame 202 is moved to the lowered position (FIGS. 6B–6C) each detector tool 212 rests on top of a respective egg 1 and clips 218 are not supported by upper plate 208. The openings 210, 211 in the upper and lower plates 208, 209 permit translational movement of the detector tools 212 to accommodate different egg sizes, shapes and orientations.

A light source 220 depends from each detector tool lower portion 214, as illustrated. Each light source 220 is configured to be positioned adjacent a portion of an egg 1 when the frame 202 is in the lowered position (FIGS. 6B–6C). The light source 220 is configured to illuminate the egg 1 with light from one or more selected portions of the spectrum. For example, the light source 220 may be configured to illuminate the egg 1 with light in the visible portion of the spectrum and/or light from the infrared portion of the spectrum.

In the illustrated embodiment, the light sources 220 included an elongated stalk 222 having a free end 22a. An opposite end 222b is secured to the detector tool 212. A light-emitting element (e.g., one or more light emitting diodes (LEDs)) 224 is positioned at the stalk free end 222a. According to embodiments of the present invention, a plurality of light-emitting elements may be positioned at the stalk free end 222a. Embodiments of the present invention are not limited to the use of LEDs. Optical fibers and light pipes may be utilized to provide light from a source.

Embodiments of the present invention are not limited to the illustrated light source 220 or to the light source 220 being secured to the detector tool 212. The light source 220 being secured to the detector tool 212. The light source 2 may be secured to various portions of the frame 202 as well as to other devices.

A cup 230 is attached to the detector tool lower portion 214, as illustrated, and is configured to overlie a portion of an egg 1 in contacting relationship therewith when the frame 202 is in the lowered position. The weight of the detector tool 212 is sufficient to seat the cup 230 on an egg such that stray light cannot enter the cup 230. Alternatively, or additionally, vacuum may be provided within the cup to facilitate seating the cup 230 on an egg 1.

A photodetector 232 is disposed within the cup 230 and is configured to generate an output signal corresponding to the intensity of light leaving an egg 1. According to embodiments of the present invention, the photodetector is provided with an integral amplifier to limit environmental electrical noise (e.g., 60 Hz from power lines). According to embodiments of the present invention, a filter may be utilized to block wavelengths other than wavelengths emitted by the light source 220. For example, if the light source 220 illuminating an egg emits 880 nM infrared light, then a reduction in sensitivity to external light (like mercury vapor lighting and fluorescent lighting) can be achieved with a photodetector module having a filter that blocks visible light. Amplifiers and filters are well known to those skilled in the art and need not be described further herein.

According to embodiments of the present invention, the cup 230 may be formed from material that shields the photodetector 232 from external light, as well as from direct light from the light source (i.e., light from the light source 220 that does not pass through the egg). An exemplary material includes, but is not limited to, silicone with a dark (e.g., black, etc.) colorant. The cup 230 may have any of various shapes and sizes and is not limited to the illustrated configuration.

In operation, a processor (e.g., controller 40, FIG. 5) communicates with the photodetector 232 in each detector tool 212 and processes an output signal generated by each photodetector 232 to identify cyclical and non-cyclical intensity variations of light passing through each egg 1. Cyclical variations in light intensity can indicate the existence of an embryo pulse, while non-cyclical variations in light intensity can indicate embryo movement.

Embodiments of the present invention are not limited to the configuration of the illustrated detector tool 212, including cup 230 and light source 220. The cup 230 may have various shapes, sizes and configurations. Moreover, the light source 220 may have various shapes, sizes and configurations. For example, multiple light sources may be associated with each detector tool 212.

Another exemplary pulse detector apparatus that may be utilized in accordance with embodiments of the present invention is the Buddy pulse detection apparatus by Avitronics (Truro, England).

Figure 7A:
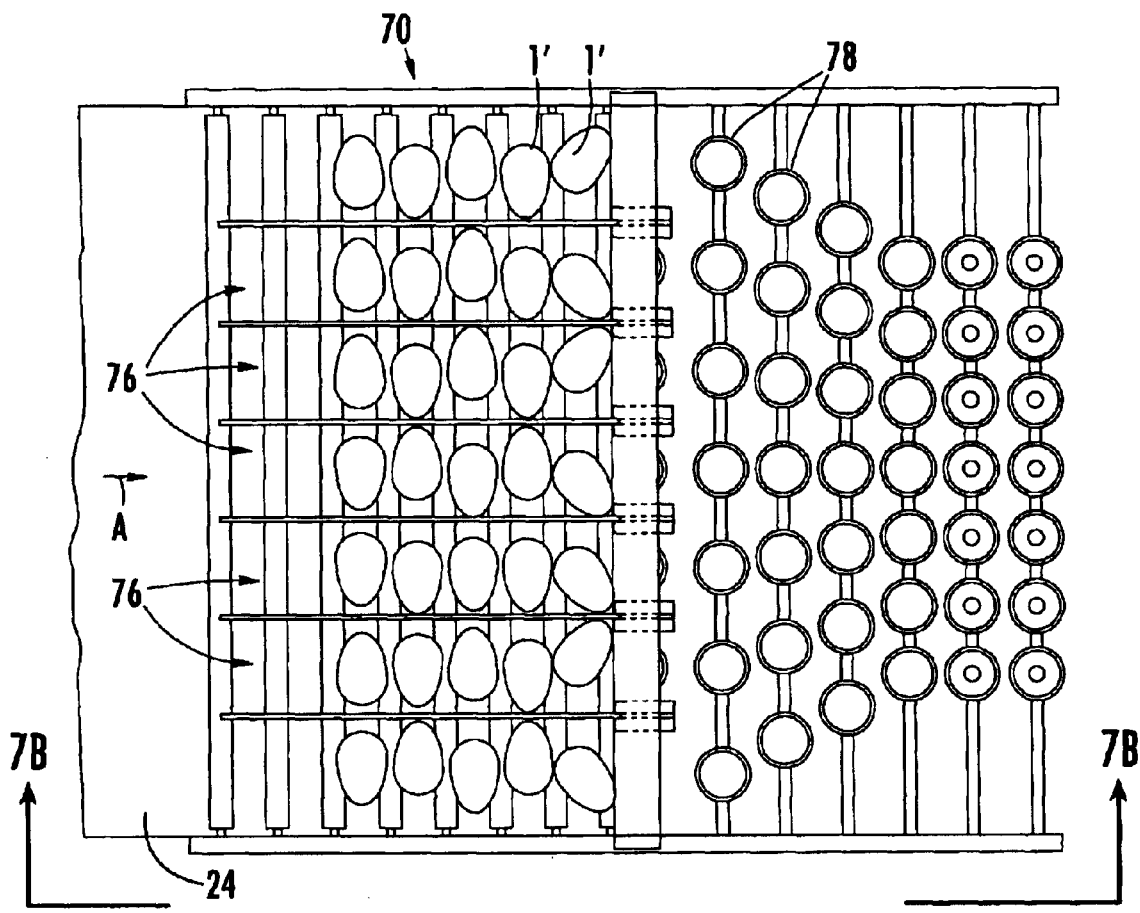
FIG. 7A is a top plan view of an egg orientation apparatus for use with a pulse detection apparatus, according to embodiments of the present invention.
Figure 7B:
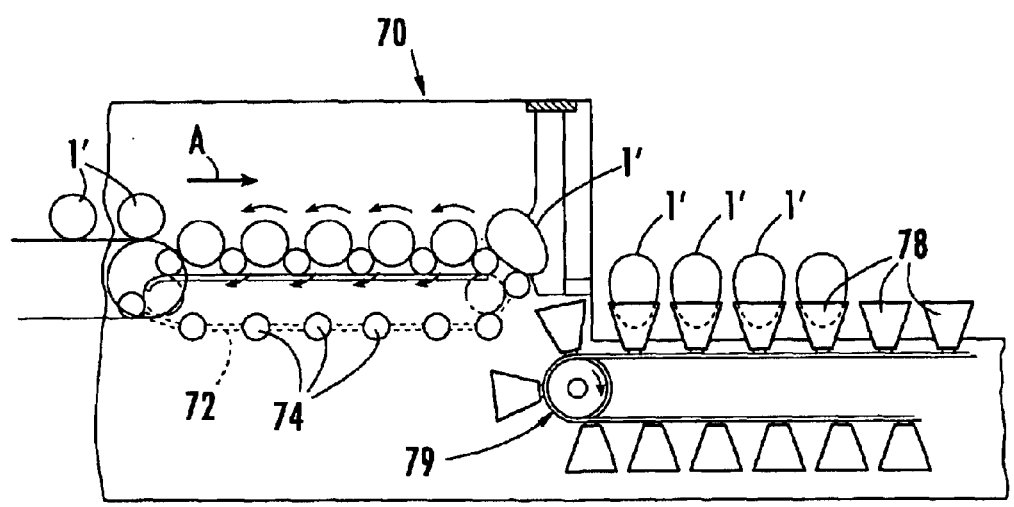
FIG. 7B is a side elevation view of the egg orientation apparatus of FIG. 7A taken along lines 7B—7B.

According to embodiments of the present invention illustrated in FIGS. 7A–7B, and egg orientation apparatus 70 may be operably associated with a pulse detection apparatus and configured to orient and hold uncertain eggs 1' in a predetermined position for pulse detection. The illustrated apparatus 70 includes an endless conveyor 72 which has a plurality of parallel rollers 74 which are rotatably connected at their ends with a drive mechanism (e.g., chains, etc.). The rollers 74 move in the direction indicated by arrow A while also rotating in the clockwise direction. Under the effect of the movement and rotation of the rollers 74, the uncertain eggs 1' travel along the direction indicated by arrow A (with their narrow ends generally perpendicular to the direction of travel indicated by arrow A) and are fed into respective channels 76 and then into respective receiving cups 78 with their narrow ends pointing downwards. The receiving cups 78 are mounted on an endless conveyor system 79 that moves the cups 78 in the direction indicated by arrow A. An exemplary egg orientation apparatus 70 is described in U.S. Pat. No. 3,592,327, which is incorporated herein by reference in its entirety. Each receiving cup 78 transports a respective uncertain egg 1' to a pulse detection station.

An egg orientation apparatus 70, according to embodiments of the present invention, may have various configurations, and is not limited to the illustrated embodiment. Different numbers of channels 76 may be utilized and receiving cups 78 of varying sizes and/or configurations may be utilized. Moreover, various types of rollers and conveyor systems may be utilized without limitation.

Exemplary spectrum generation and analysis methods and apparatus are described in U.S. Pat. No. 6,535,277 to Chalker et al., which is incorporated herein by reference in its entirety.

According to embodiments of the present invention, uncertain eggs may be placed back into egg flats via egg packing equipment. These uncertain eggs may them be subjected to human candling and then may be used to backfill positions where eggs were removed from the egg flats in the original egg stream.

Referring back to FIG. 5, uncertain eggs that are determined to be live via the recandling station 60 are transported to a backfill station 80 which places the eggs determined via recandling station 60 to be live back into a live egg flat 20 on the conveyor 22. The uncertain eggs that are confirmed to be non-live via the recandling station 60 are discarded. The backfill station 80 may be a manual station wherein eggs are manually moved or may be an automated station that moves eggs automatically and robotically.

Flat 20 at this point on the conveyor 22 contains only live eggs and can proceed to processing (e.g., inoculation, vaccine production, etc.). An exemplary device for in ovo injection of substances into a plurality of eggs in accordance with embodiments of the present invention is the INOVOJECT® automated injection system (Embrex, Inc., Research Triangle Park, North Carolina). However, any in ovo injection device may be suitable for use according to embodiments of the present invention. Suitable injection devices preferably are designed to operate in conjunction with commercial egg carrier devices or flats.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A method of rapidly and accurately identifying live eggs within a stream of eggs, comprising:
    candling each egg in the stream;
    designating each candled egg as either live, non-live, or uncertain as to whether live;
    removing eggs designated as non-live and uncertain from the stream;
    recandling each egg designated as uncertain; and
    returning recandled eggs determined to be live to the stream.

2. The method of claim 1, wherein candling each egg comprises measuring the opacity of each egg.

3. The method of claim 2, wherein measuring the opacity of each egg comprises:
    illuminating each egg with light from a light source; and
    receiving light passing through each egg at a detector positioned adjacent the egg.

4. The method of claim 2, wherein an egg is designated as live if measured opacity is less than a first threshold value, wherein an egg is designated as non-live if measured opacity is greater than a second threshold value, and wherein an egg is designated as uncertain if measured opacity is between the first and second threshold values.

5. The method of claim 1, wherein candling each egg comprises measuring the temperature of each egg.

6. The method of claim 5, wherein an egg is designated as live if measured temperature is above a first threshold temperature, wherein an egg is designated as non-live if measured temperature is lower than a second threshold temperature, and wherein an egg is designated as uncertain if measured temperature is between the first and second temperatures.

7. The method of claim 1, wherein recandling comprises determining if each egg designated as uncertain has a pulse rate, and wherein returning recandled eggs determined to be live to the stream comprises returning to the stream eggs determined to have a pulse rate.

8. The method of claim 1, wherein recandling comprises hand candling each egg designated as uncertain, and wherein returning recandled eggs determined to be live to the stream comprises returning to the stream eggs observed to have one or more of the following: red veins, an air cell at an end of the egg, or a dark embryonic area.

9. The method of claim 1, wherein recandling comprises detecting embryonic motion within each egg designated as uncertain, and wherein returning recandled eggs determined to be live to the stream comprises returning to the stream eggs having embryonic motion.

10. The method of claim 1, wherein recandling comprises:
    illuminating each egg with light from a light source, wherein the light includes light in both visible and infrared wavelengths;
    receiving light passing through the egg at a detector positioned adjacent the egg;
    determining intensity of the received light at a plurality of the visible and infrared wavelengths;
    generating a spectrum that represents light intensity at selected ones of the plurality of visible and infrared wavelengths; and
    comparing the generated spectrum with a spectrum associated with a live egg.

11. The method of claim 10, wherein returning recandled eggs determined to be live to the stream comprises returning to the stream eggs having a spectrum that substantially matches the spectrum associated with a live egg.

12. A method of rapidly and accurately identifying live eggs within a stream of eggs, comprising:
    candling each egg in the stream, comprising:
        measuring the opacity of each egg; and
        measuring the temperature of each egg;
    designating each candled egg as either live, non-live, or uncertain as to whether live based upon the measured opacity and temperature of each egg;
    removing eggs designated as non-live and uncertain from the stream;
    recandling each egg designated as uncertain; and
    returning recandled eggs determined to be live to the stream.

13. The method of claim 12, wherein measuring the opacity of each egg comprises:
    illuminating each egg with light from a light source; and
    receiving light passing through each egg at a detector positioned adjacent the egg.

14. The method of claim 13, wherein an egg is designated as live if measured opacity is less than a first threshold value, wherein an egg is designated as non-live if measured opacity is greater than a second threshold value, and wherein an egg is designated as uncertain if measured opacity is between the first and second threshold values.

15. The method of claim 12, wherein an egg is designated as live if measured temperature is above a first threshold temperature, wherein an egg is designated as non-live if measured temperature is lower than a second threshold temperature, and wherein an egg is designated as uncertain if measured temperature is between the first and second temperatures.

16. The method of claim 12, wherein recandling comprises determining is each egg designated as uncertain has a pulse rate, and wherein returning recandled eggs determined to be live to the stream comprises returning to the stream eggs determined to have a pulse rate.

17. The method of claim 12, wherein recandling comprises hand candling each egg designated as uncertain, and wherein returning recandled eggs determined to be live to the stream comprises returning to the stream eggs observed to have one or more of the following: red veins, an air cell at an end of the egg, or a dark embryonic area.

18. The method of claim 12, wherein recandling comprises detecting embryonic motion within each egg designated as uncertain, and wherein returning recandled eggs determined to be live to the stream comprises returning to the stream eggs having embryonic motion.

19. The method of claim 12, wherein recandling comprises:
    illuminating each egg with light from a light source, wherein the light includes light in both visible and infrared wavelengths;
    receiving light passing through the egg at a detector positioned adjacent the egg;
    determining intensity of the received light at a plurality of the visible and infrared wavelengths;
    generating a spectrum that represents light intensity at selected ones of the plurality of visible and infrared wavelengths; and
    comparing the generated spectrum with a spectrum associated with a live egg.

20. The method of claim 19, wherein returning recandled eggs determined to be live to the stream comprises returning to the stream eggs having a spectrum that substantially matches the spectrum associated with a live egg.

21. A system that rapidly and accurately identifies live eggs within a stream of eggs, comprising:

a conveyor configured to convey a stream of eggs;

a candling apparatus operably associated with the conveyor, wherein the candling apparatus is configured to candle each egg in the stream and to designate each candled egg as either live, non-live, or uncertain as to whether live;

an egg removal device operably associated with the conveyor that removes from the stream candled eggs designated as non-live and uncertain;

a pulse rate detection apparatus that determines if each egg designated as uncertain has a pulse rate;

an egg transfer device operably associated with the conveyor that returns to the stream eggs determined to have a pulse rate.

22. The system of claim 21, wherein the candling apparatus comprises an apparatus configured to measure the opacity of each egg, wherein an egg is designated as live if measured opacity is less than a first threshold value, wherein an egg is designated as non-live if measured opacity is greater than a second threshold value, and wherein an egg is designated as uncertain if measured opacity is between the first and second threshold values.

23. The system of claim 22, wherein the candling apparatus comprises:

a light source that illuminates each egg with light; and a detector positioned adjacent each egg that receives light passing through each egg.

24. The system of claim 21, wherein the candling apparatus comprises an apparatus configured to measure the temperature of each egg, wherein an egg is designated as live if measured temperature is above a first threshold temperature, wherein an egg is designated as non-live if measured temperature is lower than a second threshold temperature, and wherein an egg is designated as uncertain if measured temperature is between the first and second temperatures.

25. The system of claim 21, wherein the pulse rate detection apparatus is configured to detect embryonic motion, and wherein the egg transfer device returns to the stream eggs detected as having embryonic motion.

26. A system that rapidly and accurately identifies live eggs within a stream of eggs, comprising:

a conveyor configured to convey a stream of eggs;

a candling apparatus operably associated with the conveyor, wherein the candling apparatus is configured to candle each egg in the stream and to designate each candled egg as either live, non-live, or uncertain as to whether live;

an egg removal device operably associated with the conveyor that removes from the stream candled eggs designated as non-live and uncertain;

a hand candling station wherein each egg designated as uncertain is hand candled;

an egg transfer device operably associated with the conveyor that returns to the stream eggs observed to have one or more of the following: red veins, an air cell at an end of the egg, or a dark embryonic area.

27. The system of claim 26, wherein the candling apparatus comprises an apparatus configured to measure the opacity of each egg, wherein an egg is designated as live if measured opacity is less than a first threshold value, wherein an egg is designated as non-live if measured opacity is greater than a second threshold value, and wherein an egg is designated as uncertain if measured opacity is between the first and second values.

28. The system of claim 27, wherein the candling apparatus comprises:

a light source that illuminates each egg with light; and a detector positioned adjacent each egg that receives light passing through each egg.

29. The system of claim 26, wherein the candling apparatus comprises an apparatus configured to measure the temperature of each egg, wherein an egg is designated as live if measured temperature is above a first threshold temperature, wherein an egg is designated as non-live if measured temperature is lower than a second threshold temperature, and wherein an egg is designated as uncertain if measured temperature is between the first and second temperatures.

30. A system that rapidly and accurately identifies live eggs within a stream of eggs, comprising:

a conveyor configured to convey a stream of eggs;

a candling apparatus configured to candle each egg in the stream and to designate each candled egg as either live, non-live, or uncertain as to whether live;

an egg removal device operably associated with the conveyor that removes from the stream eggs designated as non-live and uncertain;

a spectrum generation and analysis apparatus, comprising:

a light source that illuminates uncertain eggs with light in both visible and infrared wavelengths;

a spectrometer that receives light passing through each uncertain egg, wherein the spectrometer obtains intensity values of the received light at selected ones of the visible and infrared wavelengths, converts light intensity values into a spectrum, and compares the spectrum with a spectrum associated with a live egg; and an egg transfer device operably associated with the conveyor that returns to the stream uncertain eggs determined to have a spectrum that substantially matches the spectrum associated with a live egg.

* * * * *